US011248228B2

(12) United States Patent
Wang et al.

(10) Patent No.: US 11,248,228 B2
(45) Date of Patent: Feb. 15, 2022

(54) METHOD FOR CONSTRUCTING NEXT-GENERATION SEQUENCING LIBRARY FOR DETECTION OF LOWFREQUENCY MUTATION AND KIT THEREOF

(71) Applicants: NANJING ANNOROAD GENE TECHNOLOGY CO. LTD, Nanjing (CN); ANNOROAD GENE TECHNOLOGY (BEIJING) CO., LTD, Beijing (CN)

(72) Inventors: Xiuli Wang, Beijing (CN); Wang Wang, Beijing (CN); Ruilin Jing, Beijing (CN); Zhaoling Xuan, Beijing (CN); Dawei Li, Beijing (CN); Junbin Liang, Beijing (CN); Chongjian Chen, Beijing (CN)

(73) Assignees: NANJING ANNOROAD GENE TECHNOLOGY CO. LTD, Beijing (CN); ANNOROAD GENE TECHNOLOGY (BEIJING) CO., LTD, Beijing (CN)

( * ) Notice: Subject to any disclaimer, the term of this patent is extended or adjusted under 35 U.S.C. 154(b) by 121 days.

(21) Appl. No.: 15/779,875

(22) PCT Filed: Mar. 28, 2016

(86) PCT No.: PCT/CN2016/077492
§ 371 (c)(1),
(2) Date: May 30, 2018

(87) PCT Pub. No.: WO2017/092204
PCT Pub. Date: Jun. 8, 2017

(65) Prior Publication Data
US 2019/0017044 A1    Jan. 17, 2019

(30) Foreign Application Priority Data

Nov. 30, 2015  (CN) .......................... 201510857393.2

(51) Int. Cl.
*C12N 15/10* (2006.01)
*C40B 40/06* (2006.01)
*C40B 50/06* (2006.01)
*C12Q 1/6809* (2018.01)
*C12Q 1/6855* (2018.01)
*C12Q 1/686* (2018.01)
*C12Q 1/6869* (2018.01)

(52) U.S. Cl.
CPC ......... *C12N 15/1068* (2013.01); *C12N 15/10* (2013.01); *C12Q 1/686* (2013.01); *C12Q 1/6809* (2013.01); *C12Q 1/6855* (2013.01); *C12Q 1/6869* (2013.01); *C40B 40/06* (2013.01); *C40B 50/06* (2013.01)

(58) Field of Classification Search
CPC .. C12N 15/1068; C12N 15/10; C12Q 1/6855; C12Q 1/686; C12Q 1/6869; C12Q 1/6809; C40B 40/06; C40B 50/06
See application file for complete search history.

(56) References Cited

FOREIGN PATENT DOCUMENTS

| CN | 102127818 A | 7/2011 | |
|---|---|---|---|
| CN | 102409049 A | 4/2012 | |
| CN | 102560688 A | 7/2012 | |
| CN | 103320521 A | 10/2013 | |
| CN | 104099666 A | 10/2014 | |
| CN | 104313172 A | 1/2015 | |
| CN | 104562213 A | 4/2015 | |
| CN | 104894651 | 9/2015 | |
| CN | 105002568 A | 10/2015 | |
| WO | WO 2015104302 | 7/2015 | |
| WO | WO2015117040 | * 8/2015 | ............. C12N 15/11 |
| WO | WO 2015172080 | 11/2015 | |

OTHER PUBLICATIONS

Flaherty et al. (Nucleic Acid Research, 2012, vol. 40, No. 1, p. 1-12, Supplemental Information, 18 pages).*
Illumina ("Illumina Adapter Sequences", Document # 1000000002694 v00, Oct. 2015, 34 pages).*
Schiemer ("Illumina TruSeq DNA Adapters De-Mystified", 2011, 5 pages).*
P. Flaherty et al: "Ultrasensitive detection of rare mutations using next-generation targeted resequencing" Nucleic Acids Research, vol. 40, No. 1, Oct. 19, 2011 (Oct. 19, 2011), pp. 1-12, XP055161679, ISSN: 0305-1048, DOI: 10.1093/nar/gkr861.
Teemu Kivioja et al: "Counting absolute numbers of molecules using unique molecular identifiers" Nature Methods, vol. 9, No. 1, Nov. 20, 2011 (Nov. 20, 2011), pp. 72-74, XP055401382, New York, ISSN: 1548-7091, DOI: 10.1038/nmeth.1778.
K. Shiroguchi et al: "Digital DNA sequencing minimizes sequence-dependent bias and amplification noise with optimized single-molecule barcodes" Proceedings of the National Academy of Sciences of the United States of America, vol. 109, No. 4, Jan. 9, 2012 (Jan. 9, 2012), pp. 1347-1352, XP055428301, ISSN: 0027-8424, DOI: 10.1073/pnas.1118018109.

* cited by examiner

Primary Examiner — Robert H Havlin
(74) Attorney, Agent, or Firm — Adam Warwick Bell; Matthew Rupert Kaser

(57) ABSTRACT

The present invention provides a method for constructing a next-generation sequencing library for detecting low-frequency mutations, and a kit thereof. The constructing method comprises steps of obtaining blunt-end DNA fragments, obtaining DNA fragments with A-tail at the 3' end, obtaining adapter-added DNA fragments using a specific nucleotide sequence and obtaining amplification products using a specific nucleotide sequence.

3 Claims, No Drawings
Specification includes a Sequence Listing.

METHOD FOR CONSTRUCTING NEXT-GENERATION SEQUENCING LIBRARY FOR DETECTION OF LOWFREQUENCY MUTATION AND KIT THEREOF

The present application claims priority from Chinese patent application No. 201510857393.2 (filing date: Nov. 30, 2015; title of the invention: Method for Constructing Second-generation Library for Detecting Low-frequency Mutation and Kit), the content of which is incorporated herein by reference in its entirety into the present specification.

A sequence listing text (.txt) file is submitted herewith under 37 CFR. 1.821(c) and is hereby incorporated by reference in its entirely. The details of the file as required under 37 CFR. 1.52(e)(5) and 37 CFR 1.77(b)(5) are as follows: Name of file is FB00031US_ST25_further_amended_NEW_OK; date of creation is Sep. 12, 2018; size is 4,096 bytes. The information recorded in electronic form (if any) submitted (under Rule 13ter if appropriate) with this application is identical to the sequence listing as contained in the application as filed.

FIELD OF THE INVENTION

The present invention relates to a method for detecting a DNA low-frequency mutation, a method for constructing a next-generation sequencing DNA library for detecting a DNA low-frequency mutation and a kit thereof, and pertains to the field of gene detection.

BACKGROUND OF THE INVENTION

Gene mutations refer to changes of base pair composition or arrangement in the structures of genes. The frequency of gene mutations is very low under natural conditions, and a low-frequency mutation refers to mutations in which the proportion of mutant DNA in the DNA sample is less than 1%. For example, it has been confirmed that there is cell-free fetal DNA in maternal plasma, free DNA of tumor characteristics in plasma of cancer patients (tumor gene mutations can be detected), virus DNA in plasma of patients with AIDS, hepatitis, etc., and there are even fragmented and a low proportion of subcloning mutant DNA in cancer tissue samples (for example, FFPE).

Because of the concentration of low-frequency mutant DNA in the sample is tiny, when the DNA low-frequency mutations are detected by a next-generation sequencing method, these DNA low-frequency mutations are often indistinguishable from amplification errors or sequencing errors, which results in a high false positive rate in the detection result. Since the low target enrichment efficiency of conventional PCR for the circulating cell-free DNA, it is difficult to achieve a great sequencing depth by increasing the amount of sequencing data and a large amount of sequencing data will be wasted. Therefore, such detection of DNA low-frequency mutations becomes a problem.

SUMMARY OF THE INVENTION

In view of the above-mentioned problems existing in the prior art, an object of the present invention is to provide a method for detecting a DNA low-frequency mutation which can effectively remove false positives, enhance enrichment efficiency of target DNA fragments and reduce a waste of sequencing data, a method for constructing a next-generation sequencing DNA library for detecting DNA low-frequency mutations and a kit thereof.

That is, the present invention includes:

1. A method for constructing a next-generation sequencing DNA library for detecting DNA low-frequency mutations, comprising:

step A: end-repairing DNA fragments to be sequenced in a sample containing low-frequency mutant DNA to obtain blunt-end DNA fragments;

step B: A-tailing of 3' end to the blunt-end DNA fragments to obtain DNA fragments with an A-tail at the 3' end;

step C: adding an adapter to the DNA fragments with an A-tail at the 3' end to obtain adapter-added DNA fragments; and step D: subjecting the adapter-added DNA fragments to PCR amplification to obtain amplification products, wherein in step C, an annealing product of a single-stranded DNA having a nucleotide sequence such as shown in SEQ ID NO: 1 and a single-stranded DNA having a nucleotide sequence such as shown in SEQ ID NO: 2 is used as the adapter;

in step D, a single-stranded DNA having a nucleotide sequence such as shown in SEQ ID NO: 3 is used as a PCR amplification primer; and the PCR amplification is conducted only once in step D in this method.

2. The method according to item 1, wherein a single-stranded DNA having a nucleotide sequence such as shown in SEQ ID NO: 4 and a single-stranded DNA having a nucleotide sequence such as shown in SEQ ID NO: 5 are further used as PCR amplification primers in step D.

3. The method according to item 1 or item 2, wherein the amount of the DNA fragments in step A is 1 to 200 ng.

4. The method according to any one of items 1 to 3, wherein the amount of the DNA fragments in step A is 5 to 50 ng.

5. The method according to any one of items 1 to 4, wherein the method further comprises a step of purifying the products between step A and step B, step C and step D, and/or after step D.

6. A kit for constructing a next-generation sequencing DNA library for detecting DNA low-frequency mutations, comprising:

a single-stranded DNA having a nucleotide sequence such as shown in SEQ ID NO: 1 and a single-stranded DNA having a nucleotide sequence such as shown in SEQ ID NO: 2, or an annealing product thereof; and a single-stranded DNA having a nucleotide sequence such as shown in SEQ ID NO: 3.

7. The kit according to item 6, further comprising one or more selected from the group consisting of T4 DNA polymerases, Klenow fragments, Klenow buffer, DNA ligase buffer, DNA ligases, Taq enzymes, dNTP, T4 polynucleotide kinases, and T4 polynucleotide kinase buffer.

8. The kit according to item 6 or item 7, which is used to perform the method according to any one items of 1 to 5.

9. The kit according to any one of items 6 to 8, further comprising a single-stranded DNA having a nucleotide sequence such as shown in SEQ ID NO: 4 and a single-stranded DNA having a nucleotide sequence such as shown in SEQ ID NO: 5.

10. A method for detecting DNA low-frequency mutations, comprising:

step A: end-repairing DNA fragments to be sequenced in a sample containing low-frequency mutant DNA to obtain a blunt-end DNA fragments;

step B: A-tailing of a 3' end to the blunt-end DNA fragments to obtain DNA fragments with an A-tail at the 3' end;

step C: adding adapter to the DNA fragments with A-tail at the 3' end to obtain adapter-added DNA fragments;

step D: subjecting the adapter-added DNA fragments to PCR amplification to obtain amplification products; and step E: conducting next-generation sequencing to the amplification products and conducting bioinformatic analysis based on the sequencing result;

wherein in step C, an annealing product of a single-stranded DNA having a nucleotide sequence such as shown in SEQ ID NO: 1 and a single-stranded DNA having a nucleotide sequence such as shown in SEQ ID NO: 2 are used as the adapter;

in step D, a single-stranded DNA having a nucleotide sequence such as shown in SEQ ID NO: 3 is used as a PCR amplification primer; and the PCR amplification is conducted only once in step D in this method.

11. The method according to item 10, wherein the next-generation sequencing is conducted by using Illumina platform.

12. The method according to item 10 or item 11, wherein a single-stranded DNA having a nucleotide sequence such as shown in SEQ ID NO: 4 and a single-stranded DNA having a nucleotide sequence such as shown in SEQ ID NO: 5 are further used as PCR amplification primers in step D.

13. The method according to any one of items 10 to 12, wherein the amount of the DNA fragments in step A is 1 to 200 ng.

14. The method according to any one of items 10 to 13, wherein the amount of the DNA fragments in step A is 5 to 50 ng.

15. The method according to any one of items 10 to 14, wherein the method further comprises a step of purifying the products between step A and step B, step C and step D, and/or after step D.

16. A kit for detecting DNA low-frequency mutations, comprising:

reagents for constructing a next-generation sequencing DNA library, and reagents for sequencing a next-generation sequencing DNA library;

wherein the reagents for constructing a next-generation DNA sequencing library comprises:

a single-stranded DNA having a nucleotide sequence such as shown in SEQ ID NO: 1 and a single-stranded DNA having a nucleotide sequence such as shown in SEQ ID NO: 2, or an annealing product thereof; and a single-stranded DNA having a nucleotide sequence such as shown in SEQ ID NO: 3.

17. The kit according to item 16, wherein the reagents for constructing a next-generation sequencing DNA library further comprises one or more selected from the group consisting of T4 DNA polymerases, Klenow fragments, Klenow buffer, DNA ligase buffer, DNA ligases, Taq enzymes, dNTP, T4 polynucleotide kinases, and T4 polynucleotide kinase buffer.

18. The kit according to item 16 or item 17, wherein the reagents for sequencing a next-generation sequencing DNA library includes one or more selected from the group consisting of resynthesis reagents, linearized P7 adapter, linearized P5 adapter, DNA polymerases, dNTP, flushing hybridization solution/buffer, 100% formamide (mass/volume), Read 2 sequencing primers for sequencing, Index i7 sequencing primers, Read 1 sequencing primers for sequencing, Hiseq Rapid PE Flow Cell, water, and reagents for enhancing photosensitivity/photographing.

19. The kit according to any one of items 16 to 18, which is used to perform the method according to any one of items 10 to 15.

20. The kit according to any one of items 16 to 19, wherein the reagents for constructing a second-generation DNA sequencing library further comprises a single-stranded DNA having a nucleotide sequence such as shown in SEQ ID NO: 4 and a single-stranded DNA having a nucleotide sequence such as shown in SEQ ID NO: 5.

Effect of the Invention

According to the present invention, a method for detecting a DNA low-frequency mutation which can effectively remove false positives, enhance enrichment efficiency of target DNA fragments and reduce waste of sequencing data, a method for constructing a next-generation sequencing DNA library for detecting DNA low-frequency mutations and a kit thereof are provided.

DETAILED DESCRIPTION OF THE INVENTION

In one aspect, the present invention provides a method for constructing a next-generation sequencing DNA library for detecting DNA low-frequency mutations (the method for constructing a library of the present invention), comprising:

step A: end-repairing DNA fragments to be sequenced in a sample containing low-frequency mutant DNA to obtain blunt-end DNA fragments;

step B: A-tailing of a 3' end to the blunt-end DNA fragments to obtain DNA fragments with an A-tail at the 3' end;

step C: adding adapters to the DNA fragments with A-tail to the 3' end to obtain adapter-added DNA fragments; and step D: subjecting the adapter-added DNA fragments to PCR amplification to obtain an amplification products, wherein in step C, an annealing product of a single-stranded DNA having a nucleotide sequence such as shown in SEQ ID NO: 1 and a single-stranded DNA having a nucleotide sequence such as shown in SEQ ID NO: 2 is used as the adapter;

in step D, a single-stranded DNA having a nucleotide sequence such as shown in SEQ ID NO: 3 is used as a PCR amplification primer; and the PCR amplification is conducted only once in step D in the method for constructing a library of the present invention.

In step D, a single-stranded DNA having a nucleotide sequence such as shown in SEQ ID NO: 4 and a single-stranded DNA having a nucleotide sequence such as shown in SEQ ID NO: 5 are further used as PCR amplification primers.

SEQ ID NO: 1 5'-TACACTCTTTCCCTA-CACGACGCTCTTCCGATCT(N)nACGCAGAGTGACT-3' (wherein n is a positive integer from 6 to 12, and n of Ns are independently selected from A, T, C, and G)

SEQ ID NO: 2 5'-GTCACTCTGCGT-3'

SEQ ID NO: 3 5'-GTGACTGGAGTTCA-GACGTGTGCTCTTCCGATCT (N) n (X) m-3' (wherein n is a positive integer from 6 to 12, and n of Ns are independently selected from A, T, C and G; m is a positive integer from 20 to 40, and m of Xs are designed to be complementary to a positive-sense strand sequence near the site to be tested (1 to 50 bp from the site, for example, 2 to 20 bp).

SEQ ID NO: 4: 5'-AATGATACGGCGACCACCGAGATC-
TACACTCTTTCCCTACACGACGCTCTTCCGATCT-3'
SEQ ID NO: 5: 5'-CAAGCAGAAGACGGCATACGAGAT
(N)₈GTGACTGGAGTTCAGACGTGTGCTCTTCCGA
TCT-3' (wherein (N)₈ is a tag sequence used to distinguish sequencing data from different samples. 8 Ns are independently selected from A, T, C and G). As the aforementioned tag sequence, for example, a tag sequence recommended by Illumina, Inc. may be used; however, it may also be designed. A person skilled in the art knows that the following principles may be considered in the design of the tag: (1) considering the problem of recognizability and recognition rate between the tag sequences, in designing the tag, the base differences must be equal to or greater than 3 bases in a 8 bp tag; (2) considering the error rate in sequence synthesis or sequencing, in designing the tag, 3 or more consecutive identical bases should be avoided in 8 bases of the tag; (3) considering that the content bias of the four bases ATGC at the same position will affect the sequencing quality in sequencing, in designing the tag, it should be ensured that the GT and AC bases are balanced at each site after the tags is mixed.

In the present description, the low-frequency mutation refers to mutations in which the proportion of mutant DNA in the DNA sample is less than 1%. Examples of the low-frequency mutant DNA include free fetal DNA in maternal plasma, free DNA of tumor characteristics in plasma of cancer patients (tumor gene mutations can be detected), virus DNA in plasma of patients with AIDS, hepatitis, etc., and fragmentation and a low proportion of subclonal mutations which even exist in cancer tissue samples (for example, FFPE).

In the method for constructing a library of the present invention, the amount of the DNA fragments in step A is not particularly limited. However, it should be noted that the method for constructing a library of the present invention can be applied to constructing a library with a small or trace amount of samples. Therefore, the amount of the DNA fragments in step A can be 1 to 200 ng, for example, 5 to 50 ng.

Preferably, in the method for constructing a library of the present invention, the PCR amplification is conducted only once in step D (for example, 10 to 30 temperature cycles may be conducted), and the method does not include any more steps of subjecting the adapter-added DNA fragments to PCR amplification. This can reduce the mismatch introduced by PCR amplification and can effectively decrease the occurrence of false positives.

Preferably, a step of purifying the products is included between step A and step B, step C and Step D, and/or after step D. The purification step can be performed by a conventional method in this technical field, for example, by magnetic beads purification. For FFPE samples, for example, they can be fragmented prior to step A.

In another aspect, the present invention provides a method for detecting DNA low-frequency mutations (the detection method of the present invention), comprising constructing a next-generation sequencing DNA library using the method for constructing a library of the present invention, conducting next-generation sequencing to the next-generation sequencing DNA library, and conducting bioinformatic analysis based on the sequencing result. In the bioinformatic analysis, it can be determined whether a certain mutation is an amplification/sequencing error or a real low-frequency mutation according to the sequence of the region in reads corresponding to (N)n of SEQ ID NO: 3 so as to reduce the false positives of the detection result.

Preferably, the sequencing in the method for detecting DNA low-frequency mutations of the present invention may be performed by, for example, using Illumina platform (e.g., HiSeq 2500 or NextSeq 500).

In another aspect, the present invention further provides a kit for constructing a next-generation sequencing DNA library, which can be used to implement the method for constructing a library of the present invention and which comprises reagents for constructing a next-generation sequencing DNA library, the reagents for constructing a next-generation sequencing DNA library including:

a single-stranded DNA having a nucleotide sequence such as shown in SEQ ID NO: 1 and a single-stranded DNA having a nucleotide sequence such as shown in SEQ ID NO: 2, or an annealing product thereof; and a single-stranded DNA having a nucleotide sequence such as shown in SEQ ID NO: 3 as a reverse primer.

Preferably, the reagents for constructing a next-generation sequencing DNA library further comprises one or more selected from the group consisting of T4 DNA polymerases, Klenow fragments, Klenow buffer, DNA ligase buffer, DNA ligases, Taq enzymes, dNTP, T4 polynucleotide kinases, and T4 polynucleotide kinase buffer.

Preferably, the reagents for constructing a next-generation sequencing DNA library further comprises a single-stranded DNA having a nucleotide sequence such as shown in SEQ ID NO: 3.

In another aspect, the present invention further provides a kit for detecting DNA low-frequency mutations, which can be used to implement the detection method of the present invention and which comprises:

reagents for constructing a next-generation sequencing DNA library, and reagents for sequencing a next-generation sequencing DNA library;

wherein the reagents for constructing a next-generation sequencing DNA library comprises:

a single-stranded DNA having a nucleotide sequence such as shown in SEQ ID NO: 1 and a single-stranded DNA having a nucleotide sequence such as shown in SEQ ID NO: 2, or an annealing product thereof;

a single-stranded DNA having a nucleotide sequence such as shown in SEQ ID NO: 3;

a single-stranded DNA having a nucleotide sequence such as shown in SEQ ID NO: 4; and a single-stranded DNA having a nucleotide sequence such as shown in SEQ ID NO: 5.

Preferably, the reagents for constructing a next-generation sequencing DNA library further comprises one or more selected from the group consisting of T4 DNA polymerases, Klenow fragments, Klenow buffer, DNA ligase buffer, DNA ligases, Taq enzymes, dNTP, T4 polynucleotide kinases, and T4 polynucleotide kinase buffer.

Preferably, the reagents for sequencing a next-generation sequencing DNA library includes one or more selected from the group consisting of resynthesis reagents, linearized P7 adapter, linearized P5 adapter, DNA polymerases, dNTP, flushing hybridization solution/buffer, 100% formamides (mass/volume), Read 2 sequencing primers for sequencing, Index i7 sequencing primers, Read 1 sequencing primers for sequencing, Hiseq Rapid PE Flow Cell, water, and reagents for enhancing photosensitivity/photographing.

Preferably, the reagents for constructing a next-generation sequencing DNA library further comprises a single-stranded DNA having a nucleotide sequence such as shown in SEQ ID NO: 4 and a single-stranded DNA having a nucleotide sequence such as shown in SEQ ID NO: 5.

EXAMPLES

The present invention will be further described in detail below combined with the examples. It should be understood that the specific examples described herein are intended to explain the present invention, rather than to limit the present invention.

Example 1 Constructing a Next-Generation Sequencing DNA Library Using the Method for Constructing a Library of the Present Invention 1. Specific Primer Design The following specific primers (equivalent to the single-stranded DNA shown in SEQ ID NO: 3) were designed, wherein PAJ408 can be used to detect AKT1 NM_001014431:c.A655C:p.T219P, PAJ410 can be used to detect TP53 NM_001126115:c.A733C:p.T245P, and PAJ 412 can be used to detect PIK3CA NM_006218:c.A3140G: p.H1047R.

TABLE 1

Specific primer sequences

| Specific primer | Primer sequence (5'-3') |
|---|---|
| PAJ408 | GTGACTGGAGTTCAGACGTGTGCTCTTCCGATCT NNNNNNNNNGGCCCTGAAGTACTCTTTCCA (SEQ ID NO: 6) |
| PAJ410 | GTGACTGGAGTTCAGACGTGTGCTCTTCCGATCT NNNNNNNNNCTACAGCCACCTGAAGTCCAAA (SEQ ID NO: 7) |
| PAJ412 | GTGACTGGAGTTCAGACGTGTGCTCTTCCGATCT NNNNNNNNNTTGTTGTCCAGCCACCAT (SEQ ID NO: 8) |

1.2 DNA Extraction

Two plasma samples were selected, cell-free DNA samples (DP13AN00374, DP13AN00375) were extracted from 2 mL plasma using a magnetic bead method and 10 ng of cell-free DNA was quantified to construct a library. The above-mentioned specific primers PAJ408, PAJ410 and PAJ412 were used to detect AKT1 NM_001014431: c.A655C:p.T219P, TP53 NM_001126115:c.A733C: p.T245P and PIK3CA NM_006218:c.A3140G:p.H1047R. For the above two samples, all the operations are the same except that the indexes used in step 1.6 are different.

1.3 End Repairing

Preparation of end repairing mix: The required reagents were taken out from a kit stored at −20° C. in advance and were placed on ice to thaw and were mixed thoroughly. Refer to Table 2 for the preparation amount of each reaction.

TABLE 2

End repairing reaction system

| Interrupted DNA sample | 41 μL |
|---|---|
| 10 × polynucleotide kinase buffer | 5 μL |
| dNTP buffer (10 mM) | 1 μL |
| T4 DNA polymerase | 1 μL |
| T4 polynucleotide kinase | 1 μL |
| Klenow fragment | 1 μL |
| ATP (10 mM) | 1 μL |
| Total volume | 50 μL |

End repairing reaction: 9 μL of mix was dispensed into a 1.5 mL centrifuge tube and the DNA sample was added to a tube. The reaction system was placed in Thermomixer for 30 minutes at 20° C. After the reaction was completed, the DNA in the reaction system was recovered and purified by using 1.8×Ampure magnetic beads and was dissolved in 32 μL EB.

1.4 A-Tailing

Preparation of A-tailing mixture: The required reagents were taken out from a kit stored at −20° C. in advance and were placed on ice to thaw and were mixed thoroughly. Refer to Table 3 for the preparation amount of each reaction.

TABLE 3

A-tailing reaction system

| Sample from the previous step | 32 μL |
|---|---|
| 10 × Blue buffer | 5 μL |
| dATP (1 mM) | 10 μL |
| Klenow fragment (lacking 3' to 5' exonuclease activity) | 3 μL |
| Total volume | 50 μL |

A-tailing reaction: 18 μL of mix was dispensed into a 1.5 mL centrifuge tube and the DNA was added to a tube. The sample was placed in Thermomixer for 30 minutes at 37° C.

1.5 Adapter Ligation

Preparation of adapter ligation mix: The required reagents were taken out from a kit stored at −20° C. in advance and were placed on ice to thaw and were mixed thoroughly. Refer to Table 4 for the preparation amount of each reaction.

TABLE 4

Adapter ligation reaction system

| Sample from the previous step | 18 μL |
|---|---|
| 2 × ligase buffer | 25 μL |
| PE Index Adapter (1 pmol/μL) | 2 μL |
| T4 DNA ligase | 5 μL |
| Total volume | 50 μL |

The PE Index Adapter is an annealing product of a single-stranded DNA as shown in SEQ ID NO: 1 and a single-stranded DNA as shown in SEQ ID NO: 2.

Adapter ligation reaction: 32 μL of mix was dispensed into a 1.5 mL centrifuge tube and the DNA was added to a tube. The sample was placed in Thermomixer for 15 minutes at 20° C. The DNA in the reaction system was purified by using 1.8×Ampure magnetic beads and was dissolved in 30 μL EB.

1.6 PCR Reaction

Preparation of PCR reaction system: The required reagents were taken out from a kit stored at −20° C. in advance and were placed on ice to thaw and were mixed uniformly. The PCR reaction system was prepared in a 0.2 mL PCR tube. Refer to Table 5 for the preparation amount of each reaction.

TABLE 5

PCR reaction system

| Sample after adding adapter and purification | 4 μL |
|---|---|
| Index-41 or 42 (10 pmol/μL) | 4 μL |

TABLE 5-continued

| PCR reaction system | |
|---|---|
| Ann common primer (10 pmol/μL) | 4 μL |
| Specific primer pool (10 pmol/μL) | 4 μL |
| 10 × buffer | 2.5 μL |
| dNTP | 2.0 μL |
| Ex taq | 0.2 μL |
| ddH$_2$O | 0.3 μL |
| Total volume | 25 μL |

Ann common primer:
(SEQ ID NO: 9)
5'-AATGATACGGCGACCACCGAGATCTACACTC
TTTCCCTACACGACGCTCTTCCGATCT-3'

Index-41 primer (for DP13AN00374):
(SEQ ID NO: 10)
5'-CAAGCAGAAGACGGCATACGAGATCGTGATGTG
TGACTGGAGTTCAGACGTGTGCTCTTCCGATCT-3'

Index-42 primer (for DP13AN00375):
(SEQ ID NO: 11)
5'-CAAGCAGAAGACGGCATACGAGATGTCAGTCGT
GTGACTGGAGTTCAGACGTGTGCTCTTCCGATCT-3'

PCR reaction: The PCR program was set up and it needs to be checked before use. The program of the PCR reaction was as follows. After the reaction, the sample was taken out timely to store at 4° C. and the program was exited or the instrument was shut down.

| 94° C. | 2 minutes | |
|---|---|---|
| 94° C. | 15 seconds | |
| 58° C. | 30 seconds | } 25 cycles |
| 72° C. | 30 seconds | |
| 72° C. | 5 minutes | |
| 4° C. | ∞ | |

1.7 Purification of the PCR Products

The PCR products in the reaction system were purified by using 0.9×Ampure magnetic beads and were dissolved in 30 μL EB.

1.8 Library Quantification

The library was subjected to 2100 Bioanalyzer (Agilent)/LabChip GX (Caliper) and QPCR tests, and passed the quality inspection.

1.9 the Constructed Library was Subjected to PE100 Sequencing Using Illumina HiSeq™ 2500.

1.10 the Finally Obtained Bioinformatic Data is Shown in the Following Table:

| Detection site | | rawdata(Mb) | Q20 | Q30 | Comparison rate | Targeted capture efficiency |
|---|---|---|---|---|---|---|
| DP13A N00374 | AKT1 c.A655C | 92.5 | 96% | 94% | 98.7% | 85.3% |
| | TP53 c.A733C | | | | | 90% |
| | PIK3CA c.A3140G | | | | | 88% |
| DP13A N00375 | AKT1 c.A655C | 107 | 96% | 94% | 98.7% | 85.7% |
| | TP53 c.A733C | | | | | 89% |
| Detection site | rawdata(Mb) | Q20 | Q30 | Comparison rate | Targeted capture efficiency |
| PIK3CA c.A3140G | | | | | 90% |

Rawdata: The amount of total data produced by sequencing;
Q20 and Q30: In high-throughput gene sequencing, each base measured provides a corresponding quality value, which measures sequencing accuracy. Q20 and Q30 in the industry indicate the percentage of the base with a quality value ≥20 or 30. The Q20 value refers to that in the base calling process of the sequencing process, the error probability of the identified base is 1%, that is, the error rate is 1%, or the accuracy is 99%. The Q30 value refers to that in the base calling process of the sequencing process, the error probability of the identified base is 0.1%, that is, the error rate is 0.1%, or the accuracy is 99.9%.

Mapping rate: the percentage of obtained sequencing data after low quality filtration aligned to a reference genome.

Target capture efficiency: the amount of data aligned to the target region divided by the amount of data aligned to the reference genome*100%, or it can be described as the percentage of the amount of data aligned to the target region accounts for from the amount of data aligned to the reference genome.

Example 2

A cell-free DNA sample (DP13AN00381) extracted from 2 mL of plasma by a magnetic bead method was selected, and 10 ng of cell-free DNA (named as DP13AN00381-1, DP13AN00381-2 and DP13AN00381-3 respectively) were quantified and taken respectively to construct the library.

For DP13AN00381-3, the same operation was performed as in the above Example 1, except that the following Index-45 was used instead of Index-41 or Index-42 in step 1.6.

Index-45:
(SEQ ID NO: 12)
5'-CAAGCAGAAGACGGCATACGAGATCAGTCGTAGTGTGACTGGAGTTC
AGACGTGTGCTCTTCCGATCT-3'

Comparative Example 1

For DP13AN00381-1 obtained in the above Example 2, the same operation was performed as in the above Example 1, except that in step 1.6, a first round PCR was conducted using a specific primer pool consisting of PAJ 413, PAJ 414 and PAJ 415 first, and after purification by magnetic beads, a second round PCR was conducted using a specific primer pool consisting of PAJ416, PAJ417 and PAJ418.

Specific Primer Sequences of the First Round PCR

| Specific primer | Primer sequence (5'-3') |
|---|---|
| PAJ413 | TGTGGGGCCGCAGTTCCAG (SEQ ID NO: 13) |

| Specific primer | Primer sequence (5'-3') |
|---|---|
| PAJ414 | CATCTCTCCTCCCTGCTTCTG (SEQ ID NO: 14) |
| PAJ415 | TGCTGTTTAATTGTGTGGAAGAT (SEQ ID NO: 15) |

Specific Primer Sequences of the Second Round PCR

| Specific primer | Primer sequence (5'-3') |
|---|---|
| PAJ416 | GTGACTGGAGTTCAGACGTGTGCTCTTCCGATCTGGCCCT GAAGTACTCTTTCCA (SEQ ID NO: 16) |
| PAJ417 | GTGACTGGAGTTCAGACGTGTGCTCTTCCGATCTCTACAG CCACCTGAAGTCCAAA (SEQ ID NO: 17) |
| PAJ418 | GTGACTGGAGTTCAGACGTGTGCTCTTCCGATCTTTGTTG TCCAGCCACCAT (SEQ ID NO: 18) |

Reaction System and Conditions of the First Round PCR:

| | |
|---|---|
| Sample after adding adapter and purification | 4 μL |
| Ann common primer (10 pmol/μL) | 4 μL |
| Specific primer pool (10 pmol/μL) | 4 μL |
| 10 × buffer | 2.5 μL |
| dNTP | 2.0 μL |
| Ex taq | 0.2 μL |
| ddH$_2$O | 6.3 μL |
| Total volume | 25 μL |

The program of the PCR reaction is as follows. After the reaction, the sample was taken out timely to store at 4° C. and the program was exited or the instrument was shut down.

| 98° C. | 30 seconds | |
| 98° C. | 10 seconds | |
| 68° C. | 30 seconds | 20 cycles |
| 72° C. | 3 minutes | |
| 4° C. | ∞ | |

The PCR product in the reaction system was recovered and purified by using 0.9×Ampure magnetic beads and was dissolved in 20 μL EB.

Reaction System and Conditions of the Second Round of PCR:

| | |
|---|---|
| Products of the first round PCR | 18 μL |
| Index-43 (10 pmol/μL) | 1 μL |
| Ann common primer (10 pmol/μL) | 1 μL |
| Specific primer pool (10 pmol/μL) | 1 μL |
| 10 × buffer | 2.5 μL |
| dNTP | 1.0 μL |
| Ex taq | 0.2 μL |
| ddH$_2$O | 0.3 μL |
| Total volume | 25 μL |

Ann common primer:

(SEQ ID NO: 9)
5'-AATGATACGGCGACCACCGAGATCTACACTCTTT CCCTACACGACGCTCTTCCGATCT-3'

Index-43:

(SEQ ID NO: 19)
5'-CAAGCAGAAGACGGCATACGAGATAGCTGCTGGT GACTGGAGTTCAGACGTGTGCTCTTCCGATCT-3'

The program of the second round PCR reaction is as follows:

| 98° C. | 30 seconds | |
| 98° C. | 10 seconds | |
| 68° C. | 30 seconds | 24 cycles |
| 72° C. | 3 minutes | |
| 4° C. | ∞ | |

Comparative Example 2

For DP13AN00381-3 obtained in the above Example 2, the same operation was performed as in the above Comparative Example 1, except that a specific primer pool consisting of PAJ408, PAJ410 and PAJ412 was used instead of the specific primer pool consisting of PAJ416, PAJ417 and PAJ418, and the following Index-44 was used instead of Index-43 for the second round PCR.

Index-44:

(SEQ ID NO: 20)
5'-CAAGCAGAAGACGGCATACGAGATCTGTCAGCGTGACTGGAGTTCAG ACGTGTGCTCTTCCGATCT-3'

For Example 2 and Comparative Examples 1 and 2, the finally obtained bioinformatic data is shown in the following table. It can be seen that the method of the present invention can effectively remove false positives, enhance enrichment efficiency of target DNA fragments and reduce waste of sequencing data.

| Sample name | Detection site | Rawdata(Mb) | Q20 | Q30 | Comparison rate | Targeted capture efficiency | Sensitivity |
|---|---|---|---|---|---|---|---|
| DP13A N00381-1 | AKT1 c.A655C | 103 | 96% | 94% | 99% | 75.3% | 1% |
| | TP53 c.A733C | | | | | 78% | 1% |
| | PIK3CA c.A3140G | | | | | 78.2% | 1% |
| DP13A N00381-2 | AKT1 c.A655C | 97 | 96% | 94% | 99% | 75.7% | 0.7% |
| | TP53 c.A733C | | | | | 77% | 0.7% |
| | PIK3CA c.A3140G | | | | | 79% | 0.7% |
| DP13A N00381-3 | AKT1 c.A655C | 105 | 96% | 94% | 99% | 87% | 0.5% |
| | TP53 c.A733C | | | | | 90.3% | 0.5% |
| | PIK3CA c.A3140G | | | | | 91% | 0.5% |

It should also be noted that any one of the technical features or combinations thereof described as constituents of a technical solution in the present specification may also be applied to other technical solutions; moreover, the technical features described as constituents of different technical solutions may also be combined in any manner to form other technical solutions on the premise that they can be practiced and do not contradict the gist of the present invention. The present invention also includes technical solutions obtained by combinations in the aforementioned cases, and these technical solutions are regarded as being described in the present specification.

The above description shows and describes preferred examples of the present invention. As mentioned above, it should be understood that the present invention is not limited to the forms disclosed herein, and should not be construed as an exclusion of other examples, but may be applied to various other combinations, modifications and environments, and may be altered within the scope of the inventive concepts described herein by the above teachings or techniques or knowledge in related fields. Alterations and variations made by the skilled person in the art without departing from the spirit and the scope of the present invention are intended to be included within the scope of the appended claims of the present invention.

INDUSTRIAL APPLICABILITY

According to the present invention, a method for detecting DNA low-frequency mutations which can effectively remove false positives, enhance enrichment efficiency of target DNA fragments and reduce waste of sequencing data, a method for constructing a next-generation sequencing DNA library for detecting DNA low-frequency mutations and a kit thereof are provided.

What is claimed is:

1. A method for constructing a DNA library for detecting DNA low-frequency mutations, comprising:
   step A: end-repairing DNA fragments to be sequenced in a sample containing low-frequency mutant DNA to obtain blunt-end DNA fragments;
   step B: A-tailing of a 3' end to the blunt-end DNA fragments to obtain DNA fragments with A-tail at the 3' end;
   step C: annealing single-stranded DNA having a nucleotide sequence of SEQ ID NO: 1 to single stranded DNA of SEQ ID NO: 2 thereby creating at least two adapters, adding the adapters to the DNA fragments with A-tail to the 3' end to obtain a first adapter-added DNA fragment and a second adapter-added DNA fragment; and
   step D: binding a single-stranded DNA target primer having a nucleotide sequence of SEQ ID NO: 3 to one of the two adapter-added DNA fragments thereby creating a primer-adapter-added DNA fragment, subjecting the primer-adapter-added DNA fragment to PCR amplification to obtain amplification products;
   wherein the PCR amplification is conducted only once in step D in this method.

2. The method according to claim 1, wherein a single-stranded DNA having a nucleotide sequence as shown in SEQ ID NO: 4 and a single-stranded DNA having a nucleotide sequence as shown in SEQ ID NO: 5 are further used as PCR amplification primers in said step D.

3. The method according to claim 1, wherein the amount of the DNA fragments in step A is 5 to 50 ng.

* * * * *

UNITED STATES PATENT AND TRADEMARK OFFICE
CERTIFICATE OF CORRECTION

PATENT NO. : 11,248,228 B2  
APPLICATION NO. : 15/779875  
DATED : February 15, 2022  
INVENTOR(S) : Xiuli Wang et al.

Page 1 of 1

It is certified that error appears in the above-identified patent and that said Letters Patent is hereby corrected as shown below:

On the Title Page

The applicants and item (73) the assignee should read:

Zhejiang Annoroad Bio-Technology Co.,Ltd.  
1/F Standard Workshop Building 2  
No. 10 Gaoxin Road, Choujiang Subdistrict  
Yiwu City, Zhejiang Province, China, 322000

And

ANNOROAD GENE TECHNOLOGY (BEIJING) CO.,LTD.  
Building B2, Yard 88, Kechuang 6 Rd  
Beijing Economic-Technological Development Area  
Beijing, China, 100176

Signed and Sealed this  
First Day of November, 2022

Katherine Kelly Vidal  
*Director of the United States Patent and Trademark Office*

SEQUENCE LISTING

```
<160> NUMBER OF SEQ ID NOS: 20

<210> SEQ ID NO 1
<211> LENGTH: 59
<212> TYPE: DNA
<213> ORGANISM: Artificial Sequence
<220> FEATURE:
<223> OTHER INFORMATION: Description of Artificial Sequence: Synthetic
      adapter sequence
<220> FEATURE:
<221> NAME/KEY: misc_feature
<222> LOCATION: (35)..(46)
<223> OTHER INFORMATION: n is independently selected from A, T, C and G,
      or n may be absent, and at least 6 nucleotides should be present
      at sites 35-46

<400> SEQUENCE: 1
tacactcttt ccctacacga cgctcttccg atctnnnnnn nnnnnnacgc agagtgact      59

<210> SEQ ID NO 2
<211> LENGTH: 12
<212> TYPE: DNA
<213> ORGANISM: Artificial Sequence
<220> FEATURE:
<223> OTHER INFORMATION: Description of Artificial Sequence: Synthetic
      adapter sequence
```

```
<400> SEQUENCE: 2
gtcactctgc gt                                                              12

<210> SEQ ID NO 3
<211> LENGTH: 86
<212> TYPE: DNA
<213> ORGANISM: Artificial Sequence
<220> FEATURE:
<223> OTHER INFORMATION: Description of Artificial Sequence: Synthetic
      primer sequence
<220> FEATURE:
<221> NAME/KEY: misc_feature
<222> LOCATION: (35)..(46)
<223> OTHER INFORMATION: n is independently selected from A, T, C and G,
      or n may be absent, and at least 6 nucleotides should be present
      at sites 35-46
<220> FEATURE:
<221> NAME/KEY: misc_feature
<222> LOCATION: (47)..(86)
<223> OTHER INFORMATION: at least 20 nucleotides should be present at
      sites 47-86, and sites 47-86 are designed to be complementary to a
      positive-sense strand sequence near the site to be tested (1 to 50
      bp from the site, for example, 2 to 20 bp)

<400> SEQUENCE: 3
gtgactggag ttcagacgtg tgctcttccg atctnnnnnn nnnnnnnnnn nnnnnnnnnn     60
nnnnnnnnnn nnnnnnnnnn nnnnnn                                          86

<210> SEQ ID NO 4
<211> LENGTH: 58
<212> TYPE: DNA
<213> ORGANISM: Artificial Sequence
<220> FEATURE:
<223> OTHER INFORMATION: Description of Artificial Sequence: Synthetic
      primer sequence

<400> SEQUENCE: 4
aatgatacgg cgaccaccga gatctacact ctttccctac acgacgctct tccgatct       58

<210> SEQ ID NO 5
<211> LENGTH: 66
<212> TYPE: DNA
<213> ORGANISM: Artificial Sequence
<220> FEATURE:
<223> OTHER INFORMATION: Description of Artificial Sequence: Synthetic
      primer sequenc
<220> FEATURE:
<221> NAME/KEY: misc_feature
<222> LOCATION: (25)..(32)
<223> OTHER INFORMATION: n is independently selected from A, T, C and G

<400> SEQUENCE: 5
caagcagaag acggcatacg agatnnnnnn nngtgactgg agttcagacg tgtgctcttc     60
cgatct                                                                66

<210> SEQ ID NO 6
<211> LENGTH: 63
<212> TYPE: DNA
<213> ORGANISM: Artificial Sequence
<220> FEATURE:
<223> OTHER INFORMATION: Description of the Artificial Sequence:
      specific primer: PAJ408
<220> FEATURE:
<221> NAME/KEY: misc_feature
<222> LOCATION: (35)..(42)
<223> OTHER INFORMATION: n is independently selected from A, T, C and G

<400> SEQUENCE: 6
```
gtgactggag ttcagacgtg tgctcttccg atctnnnnnn nnggccctga agtactcttt    60
cca                                                                 63

<210> SEQ ID NO 7
<211> LENGTH: 64
<212> TYPE: DNA
<213> ORGANISM: Artificial Sequence
<220> FEATURE:
<223> OTHER INFORMATION: Description of Artificial Sequence: specific
      primer: PAJ410
<220> FEATURE:
<221> NAME/KEY: misc_feature
<222> LOCATION: (35)..(42)
<223> OTHER INFORMATION: n is independently selected from A, T, C and G

<400> SEQUENCE: 7
gtgactggag ttcagacgtg tgctcttccg atctnnnnnn nnctacagcc acctgaagtc    60
caaa                                                                64

<210> SEQ ID NO 8
<211> LENGTH: 60
<212> TYPE: DNA
<213> ORGANISM: Artificial Sequence
<220> FEATURE:
<223> OTHER INFORMATION: Description of Artificial Sequence: specific
      primer: PAJ412
<220> FEATURE:
<221> NAME/KEY: misc_feature
<222> LOCATION: (35)..(42)
<223> OTHER INFORMATION: n is independently selected from A, T, C and G

<400> SEQUENCE: 8
gtgactggag ttcagacgtg tgctcttccg atctnnnnnn nnttgttgtc cagccaccat    60

<210> SEQ ID NO 9
<211> LENGTH: 58
<212> TYPE: DNA
<213> ORGANISM: Artificial Sequence
<220> FEATURE:
<223> OTHER INFORMATION: Description of Artificial Sequence: Ann common
      primer

<400> SEQUENCE: 9
aatgatacgg cgaccaccga gatctacact ctttccctac acgacgctct tccgatct      58

<210> SEQ ID NO 10
<211> LENGTH: 66
<212> TYPE: DNA
<213> ORGANISM: Artificial Sequence
<220> FEATURE:
<223> OTHER INFORMATION: Description of Artificial Sequence: Index-41
      primer (for DP13AN00374)

<400> SEQUENCE: 10
caagcagaag acggcatacg agatcgtgat gtgtgactgg agttcagacg tgtgctcttc    60
cgatct                                                              66

<210> SEQ ID NO 11
<211> LENGTH: 67
<212> TYPE: DNA
<213> ORGANISM: Artificial Sequence
<220> FEATURE:
<223> OTHER INFORMATION: Description of Artificial Sequence: Index-42
      primer (for DP13AN00375):

<400> SEQUENCE: 11

```
caagcagaag acggcatacg agatgtcagt cgtgtgactg gagttcagac gtgtgctctt    60
ccgatct                                                              67

<210> SEQ ID NO 12
<211> LENGTH: 68
<212> TYPE: DNA
<213> ORGANISM: Artificial Sequence
<220> FEATURE:
<223> OTHER INFORMATION: Description of Artificial Sequence: Index-45
      primer

<400> SEQUENCE: 12
caagcagaag acggcatacg agatcagtcg tagtgtgact ggagttcaga cgtgtgctct    60
tccgatct                                                             68

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: specific
      primer: PAJ413

<400> SEQUENCE: 13
tgtggggccg cagttccag                                                 19

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: specific
      primer: PAJ414

<400> SEQUENCE: 14
catctctcct ccctgcttct g                                              21

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: specific
      primer: PAJ415

<400> SEQUENCE: 15
tgctgtttaa ttgtgtggaa gat                                            23

<210> SEQ ID NO 16
<211> LENGTH: 55
<212> TYPE: DNA
<213> ORGANISM: Artificial Sequence
<220> FEATURE:
<223> OTHER INFORMATION: Description of Artificial Sequence: specific
      primer: PAJ416

<400> SEQUENCE: 16
gtgactggag ttcagacgtg tgctcttccg atctggccct gaagtactct ttcca         55

<210> SEQ ID NO 17
<211> LENGTH: 56
<212> TYPE: DNA
<213> ORGANISM: Artificial Sequence
<220> FEATURE:
<223> OTHER INFORMATION: Description of Artificial Sequence: specific
      primer: PAJ417
```

<400> SEQUENCE: 17
gtgactggag ttcagacgtg tgctcttccg atctctacag ccacctgaag tccaaa        56

<210> SEQ ID NO 18
<211> LENGTH: 52
<212> TYPE: DNA
<213> ORGANISM: Artificial Sequence
<220> FEATURE:
<223> OTHER INFORMATION: Description of Artificial Sequence: specific
      primer: PAJ418

<400> SEQUENCE: 18
gtgactggag ttcagacgtg tgctcttccg atctttgttg tccagccacc at           52

<210> SEQ ID NO 19
<211> LENGTH: 66
<212> TYPE: DNA
<213> ORGANISM: Artificial Sequence
<220> FEATURE:
<223> OTHER INFORMATION: Description of Artificial Sequence: Index-43
      primer

<400> SEQUENCE: 19
caagcagaag acggcatacg agatagctgc tggtgactgg agttcagacg tgtgctcttc   60
cgatct                                                              66

<210> SEQ ID NO 20
<211> LENGTH: 66
<212> TYPE: DNA
<213> ORGANISM: Artificial Sequence
<220> FEATURE:
<223> OTHER INFORMATION: Description of the Artificial Sequence:
      Index-44 primer

<400> SEQUENCE: 20
caagcagaag acggcatacg agatctgtca gcgtgactgg agttcagacg tgtgctcttc   60
cgatct                                                              66